United States Patent

Achhammer et al.

[11] Patent Number: 5,495,016
[45] Date of Patent: Feb. 27, 1996

[54] PREPARATION OF CAPROLACTAM

[75] Inventors: Günther Achhammer, Mannheim; Eberhard Fuchs, Frankenthal, both of Germany

[73] Assignee: BASF Aktiengesellschaft, Ludwigshafen, Germany

[21] Appl. No.: 358,411

[22] Filed: Dec. 19, 1994

[30] Foreign Application Priority Data

Nov. 25, 1994 [DE] Germany .................. 44 41 962.7

[51] Int. Cl.⁶ ............................................. C07D 201/08
[52] U.S. Cl. ............................................... 540/539
[58] Field of Search ................................... 540/539

[56] References Cited

U.S. PATENT DOCUMENTS 2,357,484  9/1944  Martin ............................ 540/539

Primary Examiner—Robert T. Bond
Attorney, Agent, or Firm—Keil & Weinkauf

[57] ABSTRACT

Caprolactam is prepared by reacting a solution of 6-aminocapronitrile with water in the liquid phase at elevated temperatures by a process in which (a) an aqueous solution of 6-aminocapronitrile in the liquid phase is heated without the addition of a catalyst in a reactor A to give a mixture I consisting essentially of water, caprolactam and a high-boiling fraction (high boiler), then (b) the water is removed from the resulting mixture I to give a mixture II consisting essentially of caprolactam and the high boilers, then (c) the caprolactam and the high boilers from mixture II are separated from one another by distillation, and then either (d1) the high boilers from stage (c) are fed into the reactor A of stage (a) or (d2) the high boilers are heated similarly to stage (a) in a further reactor B and then worked up similarly to stages (b) and (c) to give further caprolactam, or (d3) the high boilers are heated under reduced pressure in the presence of a base in a reactor C and the reacted mixture is worked up by distillation to give caprolactam.

6 Claims, No Drawings

PREPARATION OF CAPROLACTAM

The present invention relates to a process for the preparation of caprolactam by reacting 6-aminocapronitrile with water at elevated temperatures.

U.S. Pat. No. 4,628,085 describes the reaction of 6-aminocapronitrile with water in the gas phase over a special acidic silica gel (Porasil® A) at 300° C. By dilution with water, ammonia and hydrogen/nitrogen, caprolactam can be obtained in a quantitative conversion and with a selectivity of more than 95%. However, owing to deactivation, a noticeable decrease in the conversion and selectivity of at least 5% each occurs within only 150 hours.

A similar gas-phase process is described in U.S. Pat. No. 4,625,023. There, a highly dilute gas stream of 6-aminocapronitrile, adiponitrile, ammonia, water and carrier gas is passed over a silica gel and a copper/chromium/barium-titanium oxide catalyst bed. The caprolactam selectivity is 91% at 85% conversion.

Both processes have the disadvantage that the heterogeneous catalyst used is rapidly deactivated. Furthermore, a highly dilute gas stream of 6-aminocapronitrile must be reacted with water over these heterogeneous catalysts. This entails high energy costs for the evaporation and large reactor volumes.

U.S. Pat. No. 2,245,129 describes the preparation of linear polyamides by heating a 50% strength by weight aqueous solution of 6-aminocapronitrile to 200° C. for 20 hours. The formation of caprolactam is not observed here.

It is an object of the present invention to provide a process for the preparation of caprolactam from 6-aminocapronitrile, which process takes place with high selectivity in the liquid phase and without a catalyst, the intention being in particular to minimize the amount of byproducts.

We have found that this object is achieved by a process for the preparation of caprolactam by reacting 6-aminocapronitrile with water at elevated temperatures, wherein (a) an aqueous solution of 6-aminocapronitrile in the liquid phase is heated without the addition of a catalyst in a reactor A to give a mixture I consisting essentially of water, caprolactam and a high-boiling fraction (high boiler), then (b) the water is removed from the resulting mixture I to give a mixture II consisting essentially of caprolactam and the high boilers, then (c) the caprolactam and the high boilers from mixture II are separated from one another by distillation, and then either (d1) the high boilers from stage (c) are fed into the reactor A of stage (a) or (d2) the high boilers are heated similarly to stage (a) in a further reactor B and then worked up similarly to stages (b) and (c) to give further caprolactam, or (d3) the high boilers are heated under reduced pressure in the presence of a base in a reactor C and the reacted mixture is worked up by distillation to give caprolactam.

The 6-aminocapronitrile used according to the invention as a starting material is usually obtained by hydrogenating adiponitrile by a known process, for example described in DE-A 836 938, DE-A 848 654 or U.S. Pat. No. 5,151,543.

It is also possible to introduce into the reactor A mixtures which may contain essentially 6-aminocapronitrile and hexamethylenediamine, adiponitrile and/or caprolactam, as well as high-boiling fractions (high boilers) which are obtained when working up the caprolactam prepared according to the invention.

Furthermore, water is preferably used in excess; particularly preferably from 10 to 150, in particular from 20 to 100, mol of water are used per mol of 6-aminocapronitrile, to give an aqueous solution of 6-aminocapronitrile. In a further preferred embodiment, from 5 to 25 mol of water are usually used per mol of 6-aminocapronitrile, and the solution can in general be further diluted to 5–25% by weight of 6-aminocapronitrile by adding an organic solvent.

Examples of suitable solvents are:

$C_1$–$C_4$-alkanols, such as methanol, ethanol, n-propanol, isopropanol and butanols, glycols, such as ethylene glycol, diethylene glycol, triethylene glycol and tetraethylene glycol, ethers, such as methyl tert-butyl ether and diethylene glycol diethyl ether, $C_6$–$C_{10}$-alkanes, such as n-hexane, n-heptane, n-octane, n-nonane and n-decane, and cyclohexane, benzene, toluene, xylene, lactams, such as pyrrolidone and caprolactam, and N-$C_1$–$C_4$-alkyllactams, such as N-methylpyrrolidone, N-methylcaprolactam and N-ethylcaprolactam.

In a further embodiment, from 0 to 5, preferably from 0.1 to 2, % by weight of ammonia, hydrogen or nitrogen may be added to the reaction mixture.

According to the invention, the reaction in stage (a) is carried out at from 200° to 370° C., preferably from 220° to 350° C., particularly preferably from 240° to 320° C.

The reaction in stage (a) is usually carried out under super-atmospheric pressure, the pressure being chosen as a rule to be from 0.1 to 50, preferably from 5 to 25, MPa, so that the reaction mixture is preferably present as a liquid phase.

The reaction time in reactor A depends essentially on the chosen process parameters and is general from 20 to 180, preferably from 20 to 90, minutes in the continuous process. As a rule, the conversion decreases in the case of shorter reaction times, while observations to date have shown that troublesome oligomers form during longer reaction times.

The cyclization (stage (a)) is preferably carried out continuously in a reactor A, preferably in a tube reactor, in a stirred kettle or in a combination thereof.

The cyclization (stage (a)) can be carried out batchwise. In this case, the reaction time is usually from 30 to 180 minutes.

According to the invention, the discharge from reactor A is a mixture I consisting essentially of from 50 to 98, preferably from 80 to 95, % by weight of water and from 2 to 50, preferably from 5 to 20, % by weight of a mixture consisting essentially of from 50 to 90, preferably from 65 to 85, % by weight of caprolactam and from 10 to 50, preferably from 15 to 35, % by weight of a high-boiling fraction (referred to below as high boilers).

According to the invention, the water contained in mixture I is removed in stage (b) by a conventional method, preferably by distillation, to give a mixture II consisting essentially of caprolactam and the high boilers. In a preferred embodiment, a distillation is carried out under reduced pressure of from 10 to 500, preferably from 50 to 350, mbar, the vacuum distillation column used being from 2 to 20, preferably from 4 to 10, theoretical plates.

According to the invention, the mixture II obtained in stage (b) is separated by distillation in stage (c) into a caprolactam-containing fraction (top product) and a fraction containing the high boilers (bottom product). The distillation in stage (c) is preferably carried out at from 0.1 to 100, preferably from 1 to 20, mbar. Observations to date have shown that the yield of caprolactam after this distillation is from 50 to 90, preferably from 65 to 85, % by weight, based on the amount of 6-aminocapronitrile used.

According to the invention, the high boilers obtained in stage (c) can be worked up by three different methods, either in stage (d1) the high boilers from stage (c) being fed into the reactor A of stage (a) or in stage (d2) the high boilers being heated similarly to stage (a) in a further reactor B and then being worked up similarly to stages (b) and (c) to give further caprolactam, the high boilers preferably being mixed with a 5- to 25-fold, preferably a 10- to 15-fold, weight of water and then heated at from 250° to 350° C., preferably from 280° to 320° C., in reactor B in a residence time of from 30 to 120, preferably from 45 to 90, minutes, or in stage (d3) the high boilers being heated under reduced pressure, in general from 1 to 50, preferably from 1 to 10, mbar in the presence of a base, as a rule from 1 to 10, preferably from 1 to 3, % by weight thereof, in a reactor C, preferably in a tube reactor, at from 200° to 400° C., preferably from 280° to 320° C., and the reacted mixture being worked up to give further caprolactam, preferably by distillation, preferably at from 1 to 50, preferably [sic] from 1 to 10, mbar. In a preferred embodiment, a distillation column having from 2 to 20, particularly preferably from 5 to 10, theoretical plates is used.

The base used is preferably an alkali metal hydroxide, such as sodium hydroxide or potassium hydroxide, or a mixture thereof.

The advantage of the novel process is that caprolactam is obtained with high selectivity and in high yield starting from 6-aminocapronitrile in the liquid phase without a catalyst in short reaction times.

EXAMPLES

Example 1

A solution of 10% by weight of 6-aminocapronitrile (ACN) in water was heated to 300° C. in a tube reactor (volume 300 ml), the average residence time being 1 hour. No ACN was detected in the discharge. The product mixture (mixture I) contained 90% by weight of water and 10% by weight of a mixture containing 76% by weight of caprolactam and 24% by weight of high boilers. The mixture I was then distilled at from 100 to 300 mbar in a vacuum distillation column having 5 theoretical plates, ammonia-containing water being obtained as the top product and caprolactam and the high boilers being obtained at the bottom of the column (mixture II). Mixture II was separated in a further vacuum distillation column (pressure from 3 to 10 mbar) into a caprolactam fraction (top product) and a high-boiling fraction (bottom product). The caprolactam yield thus obtained was 74% by weight, since a further 2% by weight of the amount of caprolactam obtained above were converted into high boilers (essentially oligomeric lactams) during the working-up.

Example 2

The high-boiling fraction from Example 1 was mixed with a 10-fold weight of water and heated in a separate reactor for 1 hour at 300° C. The product mixture formed was worked up in the same manner as described in Example 1, 74% by weight of caprolactam being obtained, so that the total yield of caprolactam was 93% by weight, based on the amount of ACN used.

Example 3

Example 1 was repeated, and the high boilers were then recycled to the cyclization reactor (reactor A). Working up was then carried out as stated under Example 1, the total yield of caprolactam being 93% by weight.

Example 4

Example 1 was repeated. 1% by weight of solid sodium hydroxide was added to the high boilers obtained, and the mixture was heated to 300° C. under reduced pressure at 5 mbar (reactor C). At the same time, the caprolactam formed was removed continuously from the equilibrium by means of a distillation column having 5 theoretical plates. The yield of caprolactam was 74%, based on the high boilers, so that the total yield of caprolactam was 93%, based on 6-aminocapronitrile used.

We claim:

1. A process for the preparation of caprolactam by reacting a solution of 6-aminocapronitrile with water in the liquid phase at elevated temperatures, wherein (a) an aqueous solution of 6-aminocapronitrile in the liquid phase is heated without the addition of a catalyst in a reactor A to give a mixture I consisting essentially of water, caprolactam and a high-boiling fraction (high boiler), then (b) the water is removed from the resulting mixture I to give a mixture II consisting essentially of caprolactam and the high boilers, then (c) the caprolactam and the high boilers from mixture II are separated from one another by distillation, and then either (d1) the high boilers from stage (c) are fed into the reactor A of stage (a) or (d2) the high boilers are heated similarly to stage (a) in a further reactor B and then worked up similarly to stages (b) and (c) to give further caprolactam, or (d3) the high boilers are heated under reduced pressure in the presence of a base in a reactor C and the reacted mixture is worked up by distillation to give caprolactam.

2. A process as claimed in claim 1, wherein from 10 to 150 mol of water are used per mol of 6-aminocapronitrile.

3. A process as claimed in claim 1 or 2, wherein an organic solvent is added to the reaction mixture in stage (a).

4. A process as claimed in any of claims 1 to 3, wherein the reaction in reactor A is carried out at from 200° to 370° C.

5. A process as claimed in any of claims 1 to 4, wherein the reaction in reactor A is carried out at from 0.1 to 50 MPa.

6. A process as claimed in any of claims 1 to 5, wherein a residence time of from 20 to 180 minutes is maintained in reactor A.

* * * * *